US009750781B2

(12) United States Patent
Danhof

(10) Patent No.: US 9,750,781 B2
(45) Date of Patent: Sep. 5, 2017

(54) DECUBITUS TREATMENT SYSTEM

(71) Applicant: Aloe Bioscience, LLC, Dallas, TX (US)

(72) Inventor: Ivan E. Danhof, Grand Prairie, TX (US)

(73) Assignee: Aloe Bioscience, LLC, Dallas, TX (US)

( * ) Notice: Subject to any disclaimer, the term of this patent is extended or adjusted under 35 U.S.C. 154(b) by 304 days.

(21) Appl. No.: 14/579,190

(22) Filed: Dec. 22, 2014

(65) Prior Publication Data

US 2015/0140138 A1    May 21, 2015

Related U.S. Application Data

(63) Continuation of application No. 14/038,930, filed on Sep. 27, 2013, now Pat. No. 8,945,637.

(60) Provisional application No. 61/708,965, filed on Oct. 2, 2012.

(51) Int. Cl.
| | |
|---|---|
| *A61K 36/886* | (2006.01) |
| *A61K 9/00* | (2006.01) |
| *A61K 31/23* | (2006.01) |
| *A61K 47/14* | (2017.01) |

(52) U.S. Cl.
CPC .......... *A61K 36/886* (2013.01); *A61K 9/0014* (2013.01); *A61K 31/23* (2013.01); *A61K 47/14* (2013.01); *Y10S 435/81* (2013.01)

(58) Field of Classification Search
None
See application file for complete search history.

(56) References Cited

U.S. PATENT DOCUMENTS

| | | | |
|---|---|---|---|
| 5,487,899 A | 1/1996 | Davis | |
| 5,888,984 A * | 3/1999 | Brown | A61K 8/73 424/735 |
| 7,655,717 B2 | 2/2010 | Goulbourne | |
| 7,740,886 B1 | 6/2010 | Vagas | |
| 8,288,361 B2 * | 10/2012 | Della Valle | A61K 31/047 514/54 |
| 8,945,637 B2 | 2/2015 | Danhof | |
| 2002/0037312 A1 | 3/2002 | Brown et al. | |
| 2004/0013744 A1 | 1/2004 | Goulbourne | |
| 2006/0166885 A1 | 7/2006 | Van Bekkum et al. | |
| 2006/0182701 A1 | 8/2006 | Gohla et al. | |
| 2006/0257510 A1 * | 11/2006 | Della Valle | A61K 31/047 424/737 |
| 2007/0197483 A1 | 8/2007 | Inamoto | |
| 2007/0275043 A1 | 11/2007 | Freeman et al. | |
| 2008/0188546 A1 | 8/2008 | Takeda | |
| 2008/0206293 A1 | 8/2008 | Toreki et al. | |
| 2011/0021630 A1 | 1/2011 | Kepley et al. | |
| 2011/0112049 A1 | 5/2011 | Brown et al. | |
| 2011/0190722 A1 | 8/2011 | Munro et al. | |
| 2011/0269710 A1 | 11/2011 | Brown et al. | |
| 2012/0116251 A1 | 5/2012 | Ben-Shalom et al. | |
| 2014/0093593 A1 | 4/2014 | Danhof | |

FOREIGN PATENT DOCUMENTS

| | | |
|---|---|---|
| CN | 1342491 A | 4/2002 |
| CN | 101745101 A | 6/2010 |
| EP | 2903628 A1 | 8/2015 |
| WO | 2005004598 A2 | 1/2005 |
| WO | 2014055338 A1 | 4/2014 |

OTHER PUBLICATIONS

International Search Report and Written Opinion for PCT/US2013/062122, dated Dec. 2, 2013, 11 pages.
Chithra, P., et al., "Influence of Aloe vera on the glycosaminoglycans in the matrix of healing dermal wounds in rats," Journal of Ethnopharmacology, 59, Sep. 1997, pp. 179-186.
Thornfeldt, C., et al., "Cosmeceuticals Containing Herbs: Fact, Fiction, and Future," Dermatologic Surgery, 2005, vol. 31, pp. 873-880.
Hanks, J., et al., "Wound Healing in the Veterinary Rehabilitation Patient," Veterinary Clinics, Small Animal Practice Nov. 2005 US, vol. 35, No. 6, Nov. 2005, pp. 1453-1471.
Kuisma, I., et al., "Mucopolysaccharide Polysulphate Cream in the Prevention of Pressure Sores—a Double Blind Study," Original Reports, Annals of Clinical Research, vol. 19, Jan. 1987, pp. 374-377.
Matsuo, K., et al., "Case Reports of Bedsores Using Aloe Vera Gel Powder with High Molecular Weight," Pharmacognosy Research, vol. 1, Issue 3, May-Jun. 2009, pp. 136-142.
Surjushe, A., et al., "Aloe Vera: A Short Review," Indian J. Dermatol., vol. 53(4), Mar. 2008, pp. 163-166.
Thomas, D., et al., "Acemannan Hydrogel Dressing versus Saline Dressing for Pressure Ulcers," Advances in Wound Care, Oct. 1998, pp. 273-276.
Extended European Search Report and Opinion of EPO for 13843644.9 dated Mar. 23, 2016, 12 pages.
International Preliminary Report on Patentability by KIPO for PCT/US2013/062122 dated Apr. 7, 2015, 6 pages.

(Continued)

*Primary Examiner* — Chris R Tate
*Assistant Examiner* — Randall Winston
(74) *Attorney, Agent, or Firm* — Edwin S. Flores; Chalker Flores, LLP

(57) ABSTRACT

The present invention includes compositions and methods for cleaning, treating, protection and resolution of decubitus ulcers comprising: a first composition comprising a wound cleaning solution comprising aloe vera gel comprising at least 5,000 MPS, a balanced salt solution; and a second composition comprising a wound healing gel comprising aloe vera gel comprising at least 10,000 MPS, a thickening agent, and one or more preservatives and, optionally, a third composition comprising a moisture barrier cream comprising a vegetable-based emulsifier, a cosmetic ester for dry skin that has low occlusivity, an ester-based emollient that is oxidation stable and has low occlusivity; a beeswax; a hydrogenated oil, glycerin, a buffering agent, aloe vera gel comprising at least 2,000 MPS and water.

9 Claims, 3 Drawing Sheets

(56) References Cited

OTHER PUBLICATIONS

Author—Kali Dasa, Title of publication—Vaidyamanorama, Page(s) being submitted—5 (p. 4-8) (Ref. pg. No. of publication:103), Publication Date—2005, Publisher—Central Council for Research in Ayurveda & Siddha, Govt. of India, Place of Publication—New Delhi, India.†

Author—Lankapatiravana, Title of publication—Arkaprakasah, Page(s) being submitted—7 (p. 9-15) (Ref. pg. No. of publication:98), Publication Date—1995, Publisher—Krishnadas Academy, Place of Publication—Varanasi, India.†

Author—Kaiyadeva, Title of publication—Kaiyadevanighantau—(Pathyápathyávibodhaka) Edited and translated by P.V. Sharma and Guru Prasad Sharma, Page(s) being submitted—5 (p. 16-20) (Ref. pg. No. of publication:44), Publication Date—Edn. 1st, 1979, Publisher—Chaukhambha Orientalia, Place of Publication—Varanasi, India.†

\* cited by examiner
† cited by third party

Fig. 1A
Day 1
Day 20
Fig. 1B
Day 30    Fig. 1C

Fig. 2A Day 1
Fig. 2B Day 7
Fig. 2C Day 14

Day 1

Day 10

Day 14

DECUBITUS TREATMENT SYSTEM

CROSS-REFERENCE TO RELATED APPLICATIONS

This application is a continuation patent application of U.S. patent application Ser. No. 14/038,930 filed on Sep. 27, 2013 and entitled "Decubitus Treatment System," which claims priority to U.S. Provisional Application Ser. No. 61/708,965, filed Oct. 2, 2012, the entire contents of which are incorporated herein by reference.

TECHNICAL FIELD OF THE INVENTION

The present invention relates in general to the field of wound case, and more particularly, to compositions, methods and kits for treatment and maintenance of skin with or at-risk of decubitus ulcers.

STATEMENT OF FEDERALLY FUNDED RESEARCH

None.

BACKGROUND OF THE INVENTION

Without limiting the scope of the invention, its background is described in connection with wound case, and more particularly, to the treatment of decubitus ulcers.

One system for treating decubitus ulcers is taught in United States Patent Application Publication No. 2012/0116251, filed by Ben-Shalom, et al. entitled "System and Method For Preventing Decubitus Ulcers," that includes a pressure detection mat comprising a plurality of pressure-detection sensors. The mat is configured to be placed between a subject and a platform and to couple with a pressure-wound prevention system. The pressure wound prevention system is configured to receive data from the sensors within pressure detection mats, process, interpret and analyze the data, and display the analyzed data to a user. This pressure wound prevention system aims to assist in the prevention of bedsores in immobilized patients, and may be particularly useful in home care environments, acute care facilities, long term care facilities, hospices, hospitals, nursing homes, assisted living facilities and the like.

Another method for treating decubitus ulcers is taught in United States Patent Application Publication No. 2008/0188546, filed by Takeda, et al. entitled "Preventive Or Therapeutic Agents For Decubitus," that provides a preventive or preventing therapeutic agent for decubitus comprising an N-acylated derivative of hydroxyproline or a salt thereof; the above preventive or therapeutic agent wherein the N-acylated derivative of hydroxyproline or a salt thereof is contained in an amount of 0.1 to 15% by weight to the total weight; and the preventive or therapeutic agent for decubitus wherein the N-acylated group of the N-acylated derivative of hydroxyproline is an N-acylated group having 1 to 24 carbon atoms.

Yet another method for treating decubitus ulcers is taught in United States Patent Application Publication No. 2006/0166885, filed by Van Bekkum and Willem entitled "Treatment and Prevention of Decubitus," that includes a method for treating a subject suffering from, or at risk of suffering from, decubitus, the method comprising a step of administering erythropoietin (EPO), or a functional part, derivative or analogue thereof to the subject. In certain embodiments, the EPO has been recombinantly produced in host cells that further express the E1A protein of an adenovirus.

U.S. Pat. No. 7,655,717, issued to Goulbourne is entitled, "Ointment composition for treating decubitus ulcers and methods for its making and its use" and teaches an ointment composition for treating decubitus ulcers and methods for its making and its use. The composition includes a skin protestant ointment, a rash cream, an antibiotic ointment, virgin olive oil, and boric acid powder. The skin protestant ointment includes active ingredients petroleum 53.4%, lanolin 15.5%, and inactive ingredients cod liver oil containing vitamin A & vitamin D, a fragrance, light mineral oil, microcrystalline wax, and paraffin. The rash cream includes active ingredients dimethicone 1% and zinc oxide 10%, and inactive ingredients aloe barbadensis extract, benzyl alcohol, coconut oil, cod liver oil containing vitamin A & vitamin D, a fragrance, glycerol oleate, light mineral oil, ozokerite, paraffin, propylene glycol, sorbitol, synthetic beeswax, and water. The antibiotic ointment includes active ingredients polymyxin B sulfate 5,000 units, bacitracin zinc 400 units, and neomycin base (as sulfate) 3.5 mg., and an inactive ingredient white petroleum.

SUMMARY OF THE INVENTION

The present invention includes compositions, methods and kits for treatment and maintenance of skin with or at-risk of decubitus ulcers.

More particularly, in one embodiment the present invention includes a two-part composition for the cleaning, treatment, and resolution of decubitus ulcers comprising: a first composition comprising a wound cleaning solution comprising aloe vera gel comprising at least 5,000 MPS, a balanced salt solution; and a second composition comprising a wound healing gel comprising aloe vera gel comprising at least 10,000 MPS, a thickening agent, and one or more preservatives. In one aspect, the composition further comprises a third composition comprising a moisture barrier cream comprising a vegetable-based emulsifier, a cosmetic ester for dry skin that has low occlusivity, an ester-based emollient that is oxidation stable and has low occlusivity; a beeswax; a hydrogenated oil, glycerin, a buffering agent, aloe vera gel comprising at least 2,000 MPS and water. In another aspect, the balanced salt solution comprises: NaCl, KCl, $CaCl_2$, $NaHCO_3$ and $Na_2HPO_4$ adjusted to pH 4.5. In another aspect, the thickening agent comprises at least one of xanthan gum, guar gum or locust bean gum. In another aspect, one or more preservatives comprise benzoate salts, benzonium salts, or sorbate salts. In another aspect, the vegetable based emulsifier comprises a Diisostearoyl Polyglyceryl-3 Dimer Dilinoleate, a Polyglyceryl-4 Isostearate, a Polyglyceryl-4 Diisostearate, a Polyglyceryl-4 Diisostearate/Polyhydroxystearate/Sebacate or a Polyglyceryl-3 Oleate. In another aspect, the cosmetic ester for dry skin that has low occlusivity is cetearyl ethylhexanoate. In another aspect, the ester-based emollient that is oxidation stable and has low occlusivity is isocetyl Palmitate. In another aspect, the hydrogenated oil is hydrogenated castor oil.

Another embodiment of the present invention includes a method of cleaning and treating decubitus ulcers comprising: identifying a patient in need of treatment of one or more decubitus ulcers; cleaning the one or more decubitus ulcers with a first composition comprising a wound cleaning solution comprising aloe vera gel comprising at least 5,000 MPS, a balanced salt solution; and coating the one or more decubitus ulcers with a second composition comprising a wound healing gel comprising aloe vera gel comprising at least 10,000 MPS, a thickening agent, and one or more preservatives. In one aspect, the invention further comprising the step of providing the one or more decubitus ulcers with a moisture barrier with a third composition comprising a moisture barrier cream comprising a vegetable-based emulsifier, a cosmetic ester for dry skin that has low occlusivity, an ester-based emollient that is oxidation stable and has low occlusivity; a beeswax; a hydrogenated castor oil, glycerin, a buffering agent, aloe vera gel comprising at least 2,000 MPS and water. In another aspect, the balanced salt solution comprises: NaCl, KCl, $CaCl_2$, $NaHCO_3$ and $Na_2HPO_4$ adjusted to pH 4.5. In another aspect, the thickening agent comprises at least one of xanthan gum, guar gum or locust bean gum. In another aspect, the one or more preservatives comprise benzoate salts, benzonium salts, or sorbate salts. In another aspect, the vegetable based emulsifier comprises a Diisostearoyl Polyglyceryl-3 Dimer Dilinoleate, a Polyglyceryl-4 Isostearate, a Polyglyceryl-4 Diisostearate, a Polyglyceryl-4 Diisostearate/Polyhydroxystearate/Sebacate or a Polyglyceryl-3 Oleate. In another aspect, the cosmetic ester for dry skin that has low occlusivity is cetearyl ethylhexanoate. In another aspect, the ester-based emollient that is oxidation stable and has low occlusivity is isocetyl Palmitate. In another aspect, the hydrogenated oil is hydrogenated castor oil.

Another embodiment of the present invention includes a three-part composition for the cleaning, treatment, and resolution of decubitus ulcers comprising: a first composition comprising a wound cleaning solution comprising aloe vera gel comprising at least 5,000 MPS, a balanced salt solution; and a second composition comprising a wound healing gel comprising aloe vera gel comprising at least 10,000 MPS, a thickening agent, and one or more preservatives; and a third composition comprising a moisture barrier cream comprising a vegetable-based emulsifier, a cosmetic ester for dry skin that has low occlusivity, an ester-based emollient that is oxidation stable and has low occlusivity; a beeswax; a hydrogenated castor oil, glycerin, a buffering agent, aloe vera gel comprising at least 2,000 MPS and water. In one aspect, the balanced salt solution comprises: NaCl, KCl, $CaCl_2$, $NaHCO_3$ and $Na_2HPO_4$ adjusted to pH 4.5. In another aspect, the thickening agent comprises at least one of xanthan gum, guar gum or locust bean gum. In another aspect, the one or more preservatives comprise benzoate salts, benzonium salts, or sorbate salts. In another aspect, the vegetable based emulsifier comprises a Diisostearoyl Polyglyceryl-3 Dimer Dilinoleate, a Polyglyceryl-4 Isostearate, a Polyglyceryl-4 Diisostearate, a Polyglyceryl-4 Diisostearate/Polyhydroxystearate/Sebacate or a Polyglyceryl-3 Oleate. In another aspect, the cosmetic ester for dry skin that has low occlusivity is cetearyl ethylhexanoate. In another aspect, the ester-based emollient that is oxidation stable and has low occlusivity is isocetyl Palmitate. In another aspect, the hydrogenated oil is hydrogenated castor oil.

Another embodiment of the present invention includes a three-part composition for the cleaning, treatment, and resolution of decubitus ulcers comprising: a first composition consisting essentially of a wound cleaning solution comprising aloe vera gel comprising at least 5,000 MPS, a balanced salt solution; and a second composition consisting essentially of a wound healing gel comprising aloe vera gel comprising at least 10,000 MPS, a thickening agent, and one or more preservatives; and a third composition consisting essentially of a moisture barrier cream comprising a vegetable-based emulsifier, a cosmetic ester for dry skin that has low occlusivity, an ester-based emollient that is oxidation stable and has low occlusivity; a beeswax; a hydrogenated castor oil, glycerin, a buffering agent, aloe vera gel comprising at least 2,000 MPS and water.

BRIEF DESCRIPTION OF THE DRAWINGS

For a more complete understanding of the features and advantages of the present invention, reference is now made to the detailed description of the invention along with the accompanying figures and in which:

FIGS. 1A-1C show the course of treatment of patient with decubitus for day 1 (FIG. 1A); day 20 (FIG. 1B) and day 30 (FIG. 1C);

FIGS. 2A-2C show the course of treatment of patient with decubitus for day 1 (FIG. 2A); day 7 (FIG. 2B) and day 14 (FIG. 2C)

DETAILED DESCRIPTION OF THE INVENTION

Figure 3A:
FIGS. 3A-3C show the course of treatment of patient with decubitus for day 1 (FIG. 3A); day 10 (FIG. 3B) and day 14 (FIG. 3C).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "aloe vera" followed by MPS (for mucopolysaccharide) and a number (e.g., 2,000; 5,000 or 10,000) refers to a natural aloe vera gel product that has an average molecular weight distribution for long-chain polysaccharides of 2,000 saccharides molecules per chain, 5,000 saccharides per chain, and 10,000 saccharides per chain, respectively. The Aloe vera mucopolysaccharide (MPS) is a long chain sugar molecule composed of individual mannose and glucose sugar molecules connected together. There is wide range in the size of the mucopolysaccharide molecule. Therefore, Aloe 2000 refers to a composition in which the mucopolysaccharide molecules average 2,000 saccharides per chain, which can be determined using, e.g., size exclusion chromatography and gel electrophoresis.

As used herein, the term "preservative" refers to a natural or synthetic substance that is added to the present invention to prevent the growth, or decomposition of, the composition by microbes or chemical changes to the composition. Non-limiting examples of preservatives that may be optionally used with the present invention include benzoic acid and its salts, sorbic acid and its salts, calcium propionate, sodium nitrite, sodium nitrate, and sulfites (sulfur dioxide, sodium bisulfite, potassium hydrogen sulfite).

I. Wound-Wash

| | |
|---|---|
| 1. Aloe 5000 | 10.000% |
| 2. Balanced Electrolyte Solution* | 89.98% |
| 3. Citricidal | 0.020% |
| *Balanced Electrolyte Solution: | |
| 1. NaCl | 0.700% |
| 2. KCl | 0.040% |
| 3. $CaCl_2$ (anhydrous)** | 0.026% |
| 4. $NaHCO_3$ | 0.220% |
| 5. $Na_2HPO_4$ (anhydrous)** | 0.040% |

*Hydrated salt forms may be used with correction in quantity used.

Adjust product to a final pH of 4.5 with phosphoric acid.
Dispense: 4 oz. Spray Bottles II. Accelerin—Wound Healing Gel

| | |
|---|---|
| 1. *Aloe Barbadensis* Leaf Liquid (10,000 MPS)• | 97.80% |
| 2. Xanthan Gum: | 2.00% |
| 3. Potassium Sorbate: | 0.10% |
| 4. Sodium Benzoate: | 0.10% |

Dispense: 2 oz Plastic Tubes with small orifice

III. Moisture Barrier Cream

| | |
|---|---|
| Phase A | |
| 1. ISOLAN PDI | 3.00% |
| 2. TEGOSOFT Liquid | 9.500% |
| 3. TEGOSFT HP | 9.500% |
| 4. Beeswax | 0.600% |
| 5. Hydrogenated Castor Oil | 0.400% |
| Phase B | |
| 1. Glycerin USP | 3.000% |
| 2. $MgSO_4 \cdot 7\ H2O$ | 1.000% |
| 3. Purified Water | 43.000% |
| 4. Aloe 2,000 | 30.000% |
| 5. Preservatives | q.s. |
| 6. Fragrance, if any (Apple, Cinnamon, Clove) | q.s. |

Preparation
1. Heat Phase A to 80 C and add Phase B (80 C or room temperature) slowly with constant stirring.
2. Cool down and homogenize at 30 C.
Other Additives: Extracts of green tea, Lavender, Calendula, Chamomile, Allantoin.
Dispense: 2 oz Plastic tubes with small orifice.

IV. Post-Healing Skin Protectant
1. COATS Aloe Lotion/Cream: aloe vera gel, water, glycerin, allantoin, panthenol, sodium hyalurate, excipients and softeners, petrolatum, organic shea butter and preservatives (if necessary).
2. Dimethicone 1% added to above.
Dispense: 4 OZ Plastic Tubes with small orifice.

Figure 3B:
Figure 3C:

Three patients were treated using the following Decubitus Ulcer Treatment Protocol:
1. Determine the size and staging of the lesion. 2. Take a photograph of the lesion along with a small plastic: ruler for size determination. 3. Take a culture for the identification of micro-organisms and determine their pathogenic significance. 4. Irrigate the wound with normal saline. 5. Apply Wound Wash to the wound and leave in place for five minutes after which remove excess fluid with a sterile gauze sponge. 6. Apple a generous amount of Accelerin (Aloe vera Gel) and cover with a sterile 4×4 gauze sponge. 7. Apply Moisture Barrier to areas of potential involvement, especially at night to prevent urine scalds. 8. Once wound responds to the treatment protocol to a substantial degree take interval photographs. 9. Once wound is healed apply ter in die (t.i.d.) generous amounts of Aloe Protection Cream to vulnerable areas for possible cutaneous breakdown. 10. Check potential wound areas frequently based on patient's usual and favorite positions. FIGS. 1A-1C, 2A-2C, 3A-3C show the results from using the compositions, methods and protocols of the present invention. Briefly, FIGS. 1A-1C show the course of treatment of patient with decubitus for day 1 (FIG. 1A); day 20 (FIG. 1B) and day 30 (FIG. 1C). FIGS. 2A-2C show the course of treatment of patient with decubitus for day 1 (FIG. 2A); day 7 (FIG. 2B) and day 14 (FIG. 2C). FIGS. 3A-3C show the course of treatment of patient with decubitus for day 1 (FIG. 3A); day 10 (FIG. 3B) and day 14 (FIG. 3C).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

United States Patent Application Publication No. 2012/0116251
United States Patent Application Publication No. 2008/0188546
United States Patent Application Publication No. 2006/0166885
U.S. Pat. No. 7,655,717

What is claimed is:

1. A method of cleaning and treating decubitus ulcers comprising:
   identifying a subject in need thereof of treatment of one or more decubitus ulcers;
   cleaning the one or more decubitus ulcers with a first composition comprising an aloe vera mucopolysaccharide gel having an average molecular weight distribution for long-chain polysaccharides of 5,000 saccharides per chain, and a balanced salt solution; and
   coating the one or more decubitus ulcers with a second composition comprising aloe vera mucopolysaccharide gel having an average molecular weight distribution for long-chain polysaccharides of 10,000 saccharides per chain, a thickening agent, and one or more preservatives.

2. The method of claim 1, further comprising the step of providing the one or more decubitus ulcers with a moisture barrier with a third composition comprising a moisture barrier cream comprising a vegetable-based emulsifier, a cosmetic ester for dry skin that has low occlusivity, an ester-based emollient that is oxidation stable and has low occlusivity; a beeswax; a hydrogenated castor oil, glycerin, a buffering agent, aloe vera gel comprising at least 2,000 MPS and water.

3. The method of claim 1, wherein the balanced salt solution comprises: NaCl, KCl, CaCl2, NaHCO3 and Na2HPO4 adjusted to pH 4.5.

4. The method of claim 1, wherein the thickening agent comprises at least one of xanthan gum, guar gum or locust bean gum.

5. The method of claim 1, wherein one or more preservatives comprise benzoate salts, benzonium salts, or sorbate salts.

6. The method of claim 2, wherein the vegetable based emulsifier comprises a Diisostearoyl Polyglyceryl-3 Dimer Dilinoleate, a Polyglyceryl-4 Isostearate, a Polyglyceryl-4 Diisostearate, a Polyglyceryl-4 Diisostearate/Polyhydroxystearate/Sebacate or a Polyglyceryl-3 Oleate.

7. The method of claim 1, wherein the cosmetic ester for dry skin that has low occlusivity is cetearyl ethylhexanoate.

8. The method of claim 1, wherein the ester-based emollient that is oxidation stable and has low occlusivity is isocetyl Palmitate.

9. The method of claim 1, wherein the hydrogenated oil is hydrogenated castor oil.

* * * * *